United States Patent [19]

Cope et al.

[11] Patent Number: 5,700,782
[45] Date of Patent: Dec. 23, 1997

[54] ENTERAL NUTRITIONAL PRODUCT

[75] Inventors: Frederick Oliver Cope, Worthington; Linda Sue Rausch, Blacklick; Ernest William Richards, Columbus; Michelle Marie Smith, Westerville; Bonnie Chandler Abbruzzese, Dublin; Joan Marie Pero, Richmond Heights, all of Ohio

[73] Assignee: Abbott Laboratories, Abbott Park, Ill.

[21] Appl. No.: 385,389

[22] Filed: Feb. 7, 1995

Related U.S. Application Data

[63] Continuation of Ser. No. 69,067, May 28, 1993, abandoned.

[51] Int. Cl.$^6$ .................. A23J 3/16; A23J 1/20; A23L 1/052
[52] U.S. Cl. ................ 514/21; 514/2; 426/72; 426/601; 426/643; 426/648; 426/654; 426/656; 426/657
[58] Field of Search .............. 426/72, 601, 656, 426/643, 648, 654, 657; 514/2, 21

[56] References Cited

U.S. PATENT DOCUMENTS

| | | | |
|---|---|---|---|
| 4,100,024 | 7/1978 | Adler Nissen | 195/29 |
| 4,806,475 | 2/1989 | Gould | 435/165 |
| 4,871,768 | 10/1989 | Bistrian et al. | 514/547 |
| 4,906,664 | 3/1990 | Bistrian et al. | 514/552 |
| 5,053,387 | 10/1991 | Alexander | 514/2 |
| 5,081,105 | 1/1992 | Bistrian et al. | 514/2 |
| 5,085,883 | 2/1992 | Garleb et al. | 426/590 |
| 5,221,668 | 7/1993 | Henningfield et al. | 514/23 |
| 5,223,285 | 6/1993 | De Michele et al. | 426/72 |
| 5,260,279 | 11/1993 | Greenberg | 514/21 |

FOREIGN PATENT DOCUMENTS 049561  6/1992  European Pat. Off. .

OTHER PUBLICATIONS

Swenson et al Metabolism, vol. 40 No. 5 May 1991 pp. 484–490.
Karmali, "Eicosanoids in Neoplasia", Prev. Med., vol. 16(4), pp. 493–502, Jul. 1987.
Kouba, "Nutritional Care of the Individual With Cancer", Nutr. in Clin. Practice, vol. 3, pp. 175–182, Oct. 1988.

*Primary Examiner*—Chhaya D. Sayala
*Attorney, Agent, or Firm*—Lonnie R. Drayer; Thomas D. Brainard; Donald O. Nickey

[57] ABSTRACT

A liquid enteral nutritional product has been formulated which has utility, for example, for persons with cancer who are not currently undergoing radiation therapy and/or chemotherapy. The nutritional product is characterized by a fatty acid profile wherein, by weight: (a) the ratio of the sum of the n-3 to n-6 fatty acids is in the range of 1.37 to 1.70; (b) Eicosapentaenoic Acid (23:6n-3) is about 2.7–3.0% of total fatty acids.; and (c) Docosahexaenoic Acid (22:6n-3) is about 1.3–1.4% of total fatty acids. Preferably the nutritional product also contains intact protein, β-carotene, carnitine and taurine.

19 Claims, No Drawings

ENTERAL NUTRITIONAL PRODUCT

This is a Continuation of application Ser. No. 08/069,067 filed May 28, 1993 now abandoned.

The present invention relates to an enteral nutritional supplement for persons with cancer who are not currently undergoing radiation therapy and/or chemotherapy.

Cancer patients typically undergo intermittent periods of chemotherapy and/or radiation therapy during which their nutritional needs are different from the periods between therapy treatments. It is preferred that when the patient is not receiving intensive therapy a well balanced enteral diet be consumed. However, decreased appetite and changes in taste perceptions due to therapies may result in inadequate nutritional intake. Therefore, the consumption of an enteral nutritional supplement may be required.

The nutritional product of the present invention is formulated to provide enteral nutritional supplementation for a person afflicted with cancer, during a period of time when the person is not undergoing intensive chemotherapy and/or radiation therapy. That is to say, the enteral nutritional product of the present invention is intended either as a nutritional supplement, or as a sole source of nutrition. The quantity of this supplement consumed per day may be in the range of 1 to 10 8 fluid ounce servings, or as recommended by an attending physician to meet the specific metabolic needs of the patient.

During the times that a person afflicted with cancer is not undergoing intensive chemotherapy and/or radiation therapy the nutritional regimen should be one which takes into consideration the problems of diarrhea, vomiting, anorexia and damage to the intestinal architecture which can occur during such periods of therapy. For example, a nutritional product which may be used as a sole source of nutrition for a person afflicted with cancer during periods of radiation therapy and or chemotherapy is taught in commonly assigned U.S. patent application Ser. No. 8/068,919 filed on May 28, 1993 now U.S. Pat. No. 5,547,927.

Examples of commercial products which are general nutritional supplements are ENSURE® and ENSURE® WITH FIBER, both of which are available from Ross Laboratories, a Division of Abbott Laboratories, of Columbus, Ohio U.S.A. Inasmuch as the nutritional product of the present invention contains fiber, it is compared with ENSURE® WITH FIBER in Table 1 to show the major differences in the nutritional profiles of these products.

TABLE 1

| NUTRIENT | TARGET SPECIFICATIONS | | | |
|---|---|---|---|---|
| | NEW PRODUCT | | ENSURE® WITH FIBER | ENSURE® WITH FIBER |
| | In 8 Fluid Oz. | In Liter | In 8 Fluid Oz. | In Liter |
| Protein, g | 14.8 | 62.5 | 9.4 | 39.7 |
| Fat, g | 9.4 | 39.7 | 8.8 | 37.1 |
| Carbohydrate, g | 43.0 | 181.7 | 38.3 | 161.8 |
| Total Dietary Fiber, g | 2.5 | 10.6 | 3.4 | 14.4 |
| β-Carotene, µg | 1160 | 4901 | 0 | 0 |
| Folic Acid, µg | 21.0 | 88.7 | 102 | 431 |
| Carnitine, mg | 20 | 84.5 | 0 | 0 |
| Taurine, mg | 20 | 84.5 | 0 | 0 |

The nutritional product of the present invention is considerably lower in folic acid content than the general nutritional supplement because folic acid competes with some of the drugs used in cancer therapy for dihydrofolate reductase enzyme and methyl transfer. The nutritional product of the present invention contains not more than 115.3 µg per liter (27.3 µg per 8 fluid ounces), of folic acid. Put another way, the nutritional product of the present invention contains in the range of about 88.7 to 115.3 µg per liter (about 21.0–27.3 µg per 8 fluid oz.) of folic acid.

The nutritional product of the present invention contains β-carotene, carnitine and taurine, while the general nutritional supplement provides none of these nutrients. β-carotene is a carotenoid compound that has pro-vitamin A activity. However, unlike vitamin A, β-carotene is not associated with toxicity and, therefore, may be used as a source of retinol equivalents in the diet without inducing toxicity concerns. Vitamin A has been shown to reverse some of the immunosuppression associated with thermal injury and radiation injury. Favorable effects on the immune system also have been observed with β-carotene supplementation. The nutritional product of the present invention contains about 4,901 to 5,704 µg per liter (about 1,160 to 1,350 µg per 8 ounce serving) of β-carotene.

Although carnitine and taurine are present in low but adequate levels in a normal diet, these conditionally essential nutrients may become limiting under some circumstances. Carnitine deficiency has been observed in sepsis and trauma and during long-term enteral nutrition support. Evidence of taurine depletion has been demonstrated after surgical trauma and a decline in serum taurine concentrations during metabolic stress suggests that taurine supplementation is needed in that state. In humans intensive cytoxic chemotherapy is known to reduce taurine levels. The nutritional product of the present invention contains about 84.5 to 109.8 mg per liter (about 20 to 26 mg per 8 fluid ounces) of carnitine. The nutritional product of the present invention contains about 84.5 to 109.8 mg per liter (about 20 to 26 mg per 8 fluid ounces) of taurine.

As used herein and in the claims "dietary fiber" and/or "total dietary fiber" is understood to mean plant material that is undigested by human alimentary enzymes. Dietary fiber is known to be beneficial in regulating bowel function in diarrhea. Inclusion of dietary fiber in the diet also stimulates the renewal of intestinal epithelial cells and mucosal growth. The nutritional product of the present invention contains about 10.6 to 13.5 grams per liter (2.5 to 3.2 grams per 8 fluid ounces) of dietary fiber. In a preferred embodiment the dietary fiber system comprises by weight about 50% soy polysaccharide, 42.5% gum arabic, and 7.5% carboxymethylcellulose (CMC). However, any suitable source of dietary fiber may be used without varying from the scope of the invention.

The specifications for macronutrients, trace and ultratrace minerals in the nutritional product of the present invention are presented in Table 2. The specifications for vitamins and conditionally essential nutrients in the nutritional product of the present invention are presented in Table 3.

TABLE 2

MINIMUM SPECIFICATIONS FOR MACRONUTRIENTS, TRACE, AND ULTRATRACE MINERALS

| NUTRIENT | UNITS | ACCEPTABLE RANGE (Units/100 g) | TARGETS (Units/100 g) | (Units/8 oz) | (Units/Liter) |
|---|---|---|---|---|---|
| Protein | g | 5.75–5.85 | 5.69 | 14.8 | 62.5 |
| Fat | g | 3.65–3.85 | 3.62 | 9.4 | 39.7 |
| Total Dietary Fibers | g | 1.03–1.22 | 0.96 | 2.5 | 10.6 |
| Calcium | mg | 83.4–96.2 | 83.4 | 217 | 916.8 |
| Phosphorus | mg | 83.4–96.2 | 83.4 | 217 | 916.8 |
| Magnesium | mg | 32.1–38.5 | 32.1 | 83 | 350.7 |
| Sodium | mg | 79.6–97.3 | 88.5 | 230 | 971.8 |
| Potassium | mg | 124.2–151.8 | 138.5 | 360 | 1521 |
| Chloride | mg | 110.8–135.4 | 123.1 | 320 | 1352 |
| Iodine | µg | 9.6–25.8 | 9.6 | 25 | 105.6 |
| Iron | mg | 1.35–1.90 | 1.35 | 3.51 | 14.8 |
| Zinc | mg | 1.76–2.51 | 1.76 | 4.58 | 19.4 |
| Manganese | mg | 0.38–0.53 | 0.38 | 0.99 | 4.2 |
| Copper | mg | 0.16–0.22 | 0.16 | 0.42 | 1.8 |
| Selenium | µg | 5.41–8.14 | 5.38 | 14.0 | 59.2 |
| Chromium | µg | 5.92–15.3 | 5.92 | 15.4 | 65.1 |
| Molybdenum | µg | 12.4–19.2 | 12.4 | 32.2 | 136 |

TABLE 3

SPECIFICATIONS FOR VITAMINS AND CONDITIONALLY ESSENTIAL NUTRIENTS

| NUTRIENT | UNITS | MINIMUM TARGET SPECIFICATIONS (Units/Liter) | (Units/8 oz) |
|---|---|---|---|
| Vitamin A | IU | 3523 | 835 |
| β-carotene | µg | 4895 | 1160 |
| Vitamin D | IU | 282 | 66.7 |
| Vitamin E | IU | 21.1 | 5.0 |
| Vitamin K | µg | 56.1 | 13.3 |
| Folic Acid | µg | 88.7 | 21.0 |
| Niacin | mg | 14.1 | 3.34 |
| Riboflavin | mg | 1.22 | 0.29 |
| Thiamin | mg | 1.05 | 0.25 |
| Pyridoxine | mg | 1.41 | 0.33 |
| Cyanocobalamin | µg | 4.22 | 1.00 |
| Pantothenate | mg | 7.05 | 1.67 |
| Biotin | µg | 211 | 50 |
| Ascorbic Acid | mg | 211 | 50 |
| Choline | mg | 140 | 33.3 |
| Carnitine | mg | 84 | 20 |
| Taurine | mg | 84 | 20 |

The nutritional product of the present invention has a fat blend which comprises canola oil, medium chain triglycerides (MCT oil), high oleic safflower oil and fish oil. A fish oil which is suitable for use in the nutritional product of the present invention is manufactured from sardines and has been obtained from Mochida International in Shinjuku-ku, Tokyo, Japan. A disadvantage of using fish oil is that is should be stored under nitrogen with refrigeration until used to minimize oxidation and even then has a fairly short storage life. Preferably, the fish oil comprises, by weight, about 10% of the oil blend. The fish oil and canola oil are important components of the oil blend because they are rich in n-3 fatty acids. The fatty acid profile of the nutritional product of the present invention is presented in Table 4. An especially desirable feature of this fatty acid profile is that, by weight, the ratio of the sum of the n-6 fatty acids to the sum of the n-3 fatty acids is in the range of 1.37 to 1.730. Such a characteristic of the fatty acid profile is desirable because, for example, a larger portion of the fatty acids being from the n-3 group tends to result in decreased production in the cancer patient of cytokines which promote cachexia. Fat content in the nutritional product of the present invention is in the range of about 39.0 to 43.0 g per liter (9.2 to 10.1 g per 8 fluid oz.).

TABLE 4

FATTY ACID PROFILE

| FATTY ACID | % of TOTAL FATTY ACIDS (by weight) |
|---|---|
| Caprylic (8:0) | 10.3–12.1 |
| Capric (10:0) | 7.0–8.3 |
| Lauric (12:0) | about 0.2 |
| Myristic (14:0) | 0.6–0.7 |
| Palmitic (16:0) | 4.1–4.8 |
| Palmitoleic (16:1n7) | 0.9–1.0 |
| Stearic (18:0) | 1.5–1.7 |
| Oleic (18:1n-9) | 44.2–46.3 |
| Linoleic (18:2n-6) | 13.7–16.0 |
| Alpha Linolenic (18:3n-3) | 4.7–5.3 |
| Stearidonic (18:4n-3) | about 0.4 |
| Eicosenoic (20:1n-9) | 1.01–1.1 |
| Eicosapentaenoic (20:5n-3) (EPA) | 2.7–3.0 |
| Behenic (22:0) | about 0.3 |
| Erucic (22:1n-9) | 0.4–0.5 |
| Docosahexaenoic (22:1n-9) | about 0.2 |
| Docosahexaenoic (22:6n-3) (DHA) | 1.3–1.4 |
| Nervonic (24:1n-9) | 0.0–0.1 |
| Others | 0.4–1.1 |

% Total n-3 fatty acids 9.4–10.4 (by weight)
% Total n-6 fatty acids 13.7–16.0 (by weight)
% Total n-6/Total n-3 fatty acids 1.37–1.70 (by weight)
% EPA + DHA 4.0–4.4 (by weight)

Protein is provided in the nutritional product of the present invention by a combination of a soy protein isolate and sodium caseinate. A soy protein isolate that has been used to manufacture a nutritional product according to the present invention is PP750 which is a slightly hydrolyzed soy protein isolate which has obtained from Protein Technologies International, St. Louis, Mo., U.S.A.. Although the nutritional product may be manufactured using an intact soy protein isolate, the resultant viscosity of the nutritional product may be unacceptably high. The protein content of a nutritional product according to the present invention is about 55.0 to 76.0 grams per liter (13.0 to 18.0 grams per 8 fluid ounces). This level of protein is desirable in the nutritional product because it provides an excellent calorie to nitrogen ratio and high levels of all essential amino acids. The amino acid profile of the nutritional product of the present invention is presented in Table 5.

TABLE 5

AMINO ACID PROFILE

| AMINO ACID | g/100 g sample of product | g/100 g protein |
|---|---|---|
| Aspartic Acid | 0.488 | 8.34 |
| Threonine* | 0.253 | 4.32 |
| Serine | 0.343 | 5.86 |
| Glutamic Acid | 1.266 | 21.64 |
| Proline | 0.581 | 9.93 |
| Glycine | 0.141 | 2.41 |
| Alanine | 0.197 | 3.37 |
| Valine* | 0.331 | 5.66 |
| Methionine* | 0.141 | 2.41 |
| Isoleucine* | 0.271 | 4.63 |
| Leucine* | 0.538 | 9.20 |
| Tyrosine | 0.273 | 4.67 |

TABLE 5-continued

AMINO ACID PROFILE

| AMINO ACID | g/100 g sample of product | g/100 g protein |
|---|---|---|
| Phenylalanine | 0.293 | 5.01 |
| Histidine* | 0.158 | 2.70 |
| Lysine* | 0.426 | 7.28 |
| Arginine | 0.252 | 4.31 |
| Tryptophan* | 0.071 | 1.21 |
| Crystine | 0.042 | 0.72 |
| Total | 6.066 | 103.67 |
| Available Lysine | 0.380 g/100 g sample | |
| Taurine | 6.91 mg/100 g sample | |

*Essential Amino Acid
Actual protein = 5.85 g/100 g sample of product

Carbohydrates are provided in the nutritional product of the invention by sucrose and hydrolyzed cornstarch, but it is understood that any suitable source(s) of carbohydrates may be used. Preferably, the nutritional product of the present invention contains about 180 to 200 g per liter (42.5 to 47.2 g per 8 fluid oz.) of carbohydrates.

The caloric density of the nutritional product of the present invention is about 1.20 to 1.50 calories/ml, preferably about 1.30 to 1.40 calories/ml. This relatively high caloric density is desirable because it provides high caloric, vitamin and nutrient values in a low volume of the product for patients who may have reduced intake capacity.

The osmolality of the nutritional product of the present invention is about 300 to 700 mosm/kg water, preferably about 400 to 625 mosm/kg water. This osmolality value is designed to deliver low osmotic load to nutrient ratios, reducing osmotic load while delivering maximal nutrient concentration with a low risk of diarrhea.

The viscosity of the nutritional product of the present invention is about 30 to 80 cps, preferably about 40 to 65 cps. There are two embodiments of the invention disclosed herein, one of which contains oat fiber and one which does not contain oat fiber. The embodiment which contains oat fiber has a viscosity of about 30.1 to 41.0 cps, while the embodiment which does not contain oat fiber has a viscosity of about 38.9–63.2 cps. This range of viscosities allows the nutritional product to be ingested either orally or via a feeding tube (e.g. nasogastric, gastrostomy, jejunostomy, or any other suitable enteral route). This nutritional product is not designed for delivery through a central line into the bloodstream. While this nutritional product has only been manufactured in a liquid form, it is understood that it could be manufactured in a powdered form, for reconstitution with an appropriate liquid, such as water, without departing from the scope of the present invention.

MANUFACTURING PROCESS

The Bill of Materials for manufacturing a 1,000 pound batch of a nutritional product in accordance with the invention is presented in Table 6. It is understood that this Bill of Materials has been used to make a nutritional product in accordance with the present invention, but could be altered in ingredients and quantities of ingredients without varying from the scope of the present invention.

TABLE 6

BILL OF MATERIALS

| INGREDIENT | AMOUNT for 454 Kg (1000 lbs) |
|---|---|
| Canola oil | 81.4 kg (17.934 lbs.) |
| MCT oil | 3.26 kg (7.174 lbs.) |
| High Oleic Safflower Oil | 3.26 kg (7.174 lbs.) |
| Soy Lecithin | 0.74 kg (1.620 lbs.) |
| Oil Soluble Vitamin Premix | 24.60 g. |
| Vitamin D3 | 0.158 g. |
| Vitamin E | 17.67 g. |
| Vitamin K | 0.033 g. |
| Vitamin A palmitate | 2.000 g. |
| $\beta^1$-Carotene | 9.790 g. |
| Fish Oil | 1.64 kg (3.587 lbs.) |
| Soy Polysaccharide* | 1.08 kg (2.373 lbs.) |
| Gum Arabic | 2.10 kg (4.623 lbs.) |
| Carboxymethylcellulose | 362.87 g. |
| Soy Protein Isolate | 5.82 kg (12.829 lbs.) |
| Sodium Caseinate | 22.72 kg (50.036 lbs.) |
| Water | 315.21 kg (694.289 lbs.) |
| Oat Fiber* | 1.42 kg (3.133 lbs.) |
| Magnesium Chloride | 0.73 kg (1.601 lbs.) |
| Potassium Citrate | 0.99 kg (2.176 lbs.) |
| Potassium Chloride | 351.50 g. |
| Potassium Iodide | 0.057 g. |
| UTM/TM Premix | 103.20 g. |
| Zinc | 8.548 g. |
| Iron | 6.504 g. |
| Manganese | 1.815 g. |
| Copper | 0.767 g. |
| Selenium | 0.028 g. |
| Chromium | 0.031 g. |
| Molybdenum | 0.060 g. |
| Magnesium Phosphate | 296.81 g. |
| Calcium Carbonate | 427.02 g. |
| Tricalcium Phosphate | 0.65 kg (1.437 lbs.) |
| Sucrose | 11.92 kg (26.250 lbs.) |
| Hydrolyzed Cornstarch | 71.09 kg (156.580 lbs.) |
| Ascorbic Acid | 207.00 g. |
| Choline Chloride | 82.0 g. |
| L-Carnitine | 40.00 g. |
| Taurine | 40.00 g. |
| Vitamins and Conditionally Essential Nutrients (minimum amount per liter of product) | |
| Folic Acid | 88.7 µg |
| Niacin | 14.1 mg |
| Riboflavin | 1.22 mg |
| Thiamine | 1.05 mg |
| Pyridoxine | 1.41 mg |
| Cyanocobalamine | 4.22 µg |
| Pantothenate | 7.05 mg |
| Biotin | 211.00 µg |
| Natural and Artifical Vanilla** | 0.68 kg (1.500 lbs.) |
| Artificial Creamy Vanilla** | 0.45 kg (1.000 lbs.) |
| Artificial Strawberry*** | 362.87 g. |
| FDC Red #3*** | 18.14 g. |

*In an alternative formulation no oat fiber is used and the quantity of soy polysaccharide is increased to 2.69 kg (5.931 pounds).
**These ingredients are used only when making a vanilla flavored product.
***These ingredients are included only when making a strawberry flavored product.

A nutritional product in accordance with the present invention has been produced using the preceding Bill of Materials and the manufacturing process described below. However, it is understood that the manufacturing process may be altered based upon available equipment and other variables.

An oil blend containing dietary fiber is prepared by the following procedure. The canola oil, medium chain triglycerides and high oleic safflower oil are placed together in a blend tank and the resulting oil blend is heated to a temperature in the range of about 43°–52° C. (110°–125° F.). The soy lecithin, oil soluble vitamin premix, Vitamin A palmitate and beta carotene are added to the oil blend. While maintaining the temperature of the oil blend in the range of 43°–52° C. (110°–125° F.) the fish oil is added thereto. Add the soy polysaccharide to the oil blend, and agitate the oil blend thoroughly. Add the gum arabic to the oil blend, and mix the oil blend until no clumping appears. Add the carbomethylcellulose to the oil blend, and mix until the blend is uniformly dispersed, without any clumping. Add about 70% of the soy protein isolate to the blend. Adding some of the soy protein isolate to the oil blend instead of putting all of the soy protein isolate in the protein slurry facilitates easier mixability of the protein slurry while maintaining the oil blend at a pumpable viscosity level. Maintain the resultant oil blend with fiber at a temperature in the range of about 43°–52° C. (110°–125° F.), with agitation, until it is combined with additional product ingredients.

A protein slurry is prepared by the following procedure. Place about 199.3 kg (439 pounds) of water in a vessel and heat the water to a temperature in the range of about 60°–71° C. (140°–160° F.). Add the oat fiber to the water. When the oat fiber has been dispersed, add the sodium caseinate to the heated water. After the protein has dissolved, maintain the temperature of the resultant slurry in the range of about 43°–54° C. (110°–130° F.). Add the remainder of the soy protein isolate to the slurry, and continue to maintain the slurry at a temperature in the range of about 43°–54° C. (110°–130° F.) until it is combined with additional product ingredients.

An oat fiber which is suitable for use in the practice of the present invention comprises ground up oat hulls that have been treated in the manner taught in U.S. Pat. No. 4,806,875, and may be obtained from Opta Food Ingredients, Inc. of Cambridge, Mass., U.S.A.

In an alternative embodiment the oat fiber is eliminated and, as indicated in the Bill of Materials, a larger quantity of soy polysaccharide is used. In such an alternative embodiment only about 30% of the soy protein isolate is added to the oil blend and the remainder of the soy protein isolate is added to this protein slurry. If there is no oat fiber in the formulation, but more soy polysaccharide, (all of which must be added to the oil blend), not as much soy protein isolate can be accommodated in the oil blend, so more soy protein isolate is added to the protein slurry in place of the oat fiber. These adjustments facilitate maintaining the mixability and pumpability of the blends and slurries.

A carbohydrate/mineral slurry is prepared by the following procedure. Place about 71.7 kg (158 pounds) of water in a vessel and heat the water to a temperature in the range of about 60°–71° C. (140°–160° F.). (Note in the all-soy polysaccharide alternative embodiment about 62.2 kg (137 lbs) of water is used.) Add to the water the magnesium chloride, potassium citrate, potassium chloride and potassium iodide. Agitate the resultant mixture until these ingredients have been dissolved/suspended, and the mixture is uniform in appearance. Add the ultra trace mineral/trace mineral (UTM/TM) premix to the mixture. (Preferably the UTM/TM premix contains zinc sulfate, ferrous sulfate, manganese sulfate, copper sulfate, sodium selenite, chromium chloride, sodium molybdate and citric acid, with sucrose used as a diluent). At this time the slurry should be green in color. The magnesium phosphate, calcium carbonate and tricalcium phosphate are then added to the slurry. The sucrose and hydrolyzed cornstarch are added to the slurry, and the slurry is agitated until these ingredients have been dissolved. The resultant carbohydrate/mineral slurry is continuously agitated and maintained at a temperature in the range of about 60°–71° C. (140°–160° F.) until it is combined with additional product ingredients.

The three slurries/blends which have been prepared are then blended together by the following procedure. Combine the protein slurry with the oil blend containing dietary fiber with agitation. To the resultant blend add the carbohydrate/mineral slurry, and mix the blend thoroughly. Adjust the temperature of the resultant product blend to be in the range of about 49°–57° C. (120°–135° F.). The pH of the product blend should be in the range of 6.45–6.70, and if necessary 1N potassium hydroxide is added to bring the pH of the product blend into the specified range.

The product blend is processed as follows:

(a) The product blend is heated to a temperature in the range of about 68°–74° C. (155°–165° F.).

(b) The product blend is deaerated at 10–15 in Hg.

(c) The product blend is emulsified with a homogenizer at about 900–1100 psig.

(d) The product blend is heated to a temperature in the range of about 120°–122° C. (248°–252° F.).

(e) The product blend is heated by steam injection to a temperature in the range of about 144°–148° C. (292°–298° F.) and held at this temperature for about 5 seconds.

(f) The product blend is flash cooled to a temperature in the range of about 120°–122° C. (248°–252° F.).

(g) The product blend is further cooled to a temperature in the range of about 71°–79° C. (160°–175° F.).

(h) The product blend is homogenized at 3,900–4,100/ 400–600 psig.

(i) The product blend is held at a temperature in the range of about 74°–85° C. (165°–185° F.) for 16 seconds.

(j) The product blend is cooled to a temperature in the range of about 1°–7° C. (33°–44° F.), and stored at this temperature to minimize microbial growth until further ingredients are added thereto.

It is recommended that if the nutritional product of the present invention is manufactured on a large scale that rather than adding the fish oil to the oil blend, the fish oil should be metered into the product blend at a constant rate just prior to emulsification to improve dispersion of the fish oil throughout the final blend.

At the time that the vitamins and flavors are added to the blend dilution water is added to the blend. If a vanilla flavored product is being produced add 27.4 kg (60.3 lbs) of dilution water; if a strawberry flavored product is being produced add 33.1 kg (73.0 lbs) of dilution water.

A vitamin solution is prepared by the following procedure. About 9.2 kg (20.3 pounds) of water is placed in a vessel and adjusted to a temperature in the range of about 10°–43° C. (50°–110° F.). The ascorbic acid is added to the water which is agitated until the ascorbic acid is dissolved therein. The resultant solution is neutralized with 45% potassium hydroxide. The choline chloride, L-carnitine and taurine are added to the solution and blended until dissolved. Add the following water soluble vitamins to the solution: niacinamide, d-Ca Pantothenoic acid, biotin, pyridoxine HCL, folic acid, thiamine HCL, cyanocobalamin, and riboflavin (note that it would be desirable to provide the water soluble vitamins in a premix, but such a premix was not yet developed at the time of filing a patent application for the new nutritional product disclosed herein). The pH of the resultant solution should be in the range of about 6.0–10.0. The vitamin solution is then added to the product blend.

A flavor solution is prepared and added to the product blend with agitation. If a vanilla flavored product is being manufactured, add (a) the natural and artificial vanilla and (b) the artificial creamy vanilla to 10.2 kg (22.5 lbs) of water. If a strawberry flavored product is being manufactured add the artificial strawberry to 3.3 kg (7.2 lbs) of water.

If a strawberry flavored product is being manufactured, a color-in water solution is prepared by mixing the FD&C Red #3 in about 1.8 kg (4 pounds) of water. The color-in-water solution is then added to the product blend with agitation.

The resultant nutritional product of the present invention may then be placed in suitable containers, for example 8 ounce cans, which are then sealed with suitable closures. The product should be sealed in containers within 48 hours after completion of the standardization/flavoring procedures. The nutritional product may then be sterilized using suitable procedures which are well known in the art.

We claim:

1. A liquid enteral nutritional product comprising per liter:
   (a) about 55 to about 76 g of protein;
   (b) about 39 to about 43 g of fat, said fat having a fatty acid profile such that, by weight:
      (i) the ratio of the sum of the n-6 fatty acids to the sum of the n-3 fatty acids ranges from about 1.37 to about 1.70;
      (ii) eicosapentaenoic acid (20:5 n-3) constitutes about 2.7 to 3.0% of total fatty acids;
      (iii) docosahexaenoic acid (22:6 n-3) constitutes about 1.3 to 1.4% of total fatty acids; and
      (iv) oleic acid (18:1 n-9) constitutes about 44.2 to 46.3% of total fatty acids;
   (c) about 180 to about 200 g of carbohydrate;
   (d) about 10.6 to about 13.5 g of dietary fiber;
   (e) about 88.7 to about 115.3 µg of folic acid;
   (f) about 4.9 to about 5.7 mg of β-carotene;
   (g) about 84.5 to about 109.8 mg of carnitine; and
   (h) about 84.5 to about 109.8 mg of taurine.

2. The nutritional product of claim 1 wherein said protein is selected from sodium caseinate, soy protein isolate and mixtures thereof.

3. The nutritional product as described in claim 1 wherein said dietary fiber is selected from soy polysaccharide, gum arabic, carboxymethylcellulose, oat fiber and mixtures thereof.

4. The nutritional product of claim 1 wherein said fat includes fish oil.

5. The nutritional product of claim 4 wherein said fat further includes at least one of canola oil, medium chain triglycerides, high oleic safflower oil and mixtures thereof.

6. The nutritional product of claim 4 wherein said protein comprises a mixture of sodium caseinate and soy protein isolates; said fat further includes a mixture of canola oil, medium chain triglycerides and high oleic safflower oil; and said dietary fiber comprises a mixture of soy polysaccharide, gum arabic, carboxymethylcellulose and oat fiber; and wherein the caloric density of said product is between about 1.20 and about 1.50 calories/ml.

7. The nutritional product of claim 4 wherein said protein is selected from sodium caseinate, soy protein isolates and mixtures thereof; wherein said fat further includes at least one of canola oil, medium chain triglycerides, high oleic safflower oil and mixtures thereof; and wherein said dietary fiber is selected from soy polysaccharide, gum arabic, carboxymethylcellulose, oat fiber and mixtures thereof.

8. The nutritional product of claim 7 wherein the caloric density of said product is between about 1.20 and about 1.50 calories/ml.

9. The nutritional product of claim 1 wherein the caloric density of said product is between about 1.20 and about 1.50 calories/ml.

10. A method of providing nutritional support to a person who is afflicted with cancer, said method comprising enterally administering to said person a liquid nutritional product according to claim 1.

11. The method of claim 10 wherein the protein in said liquid nutritional product is selected from sodium caseinate, soy protein isolates and mixtures thereof.

12. The method of claim 10 wherein the dietary fiber in said liquid nutritional product is selected from soy polysaccharide, gum arabic, carboxymethylcellulose, oat fiber and mixtures thereof.

13. The method of claim 10 wherein the fat in said liquid nutritional product includes fish oil; and additionally at least one of canola oil, medium chain triglycerides, high oleic safflower oil and mixtures thereof.

14. The method of claim 13 wherein said protein comprises a mixture of sodium caseinate and soy protein isolates; said fat includes a mixture of fish oil, canola oil, medium chain triglycerides and high oleic safflower oil; and said dietary fiber comprises a mixture of soy polysaccharide, gum arabic, carboxymethylcellulose and oat fiber; and wherein the caloric density of said product is between about 1.20 and about 1.50 calories/ml.

15. The method of claim 13 wherein said protein is selected from sodium caseinate, soy protein isolates and mixtures thereof; and wherein said dietary fiber is selected from soy polysaccharide, gum arabic, carboxymethylcellulose, oat fiber and mixtures thereof.

16. The method of claim 15 wherein the caloric density of said product is between about 1.20 and about 1.50 calories/ml.

17. The method of claim 10 further comprising enterally administering said liquid nutritional product during periods when said person afflicted with cancer is not undergoing radiation therapy or chemotherapy.

18. The method of claim 10 further comprising enterally administering from 1 to about 10 eight fluid ounce servings per day of said liquid nutritional product.

19. The method of claim 18 wherein said enteral administration of said liquid nutritional product is supplemental to said person's diet.

* * * * *